United States Patent [19]

Fujieda et al.

[11] Patent Number: 5,352,889
[45] Date of Patent: Oct. 4, 1994

[54] POSITIONING MECHANISM OF OPHTHALMOLOGIC APPARATUS

[75] Inventors: Masanao Fujieda, Toyohashi; Noriji Kawai, Gamagori, both of Japan

[73] Assignee: Nidek Co., Ltd., Gamagori, Japan

[21] Appl. No.: 76,745

[22] Filed: Jun. 15, 1993

[30] Foreign Application Priority Data

Jun. 30, 1992 [JP]  Japan .................................. 4-197519

[51] Int. Cl.$^5$ .............................................. G01D 5/34
[52] U.S. Cl. ...................................... 250/229; 341/161
[58] Field of Search ............... 250/229, 231.13, 222.1, 250/221, 237 G; 345/161

[56] References Cited

U.S. PATENT DOCUMENTS 4,442,351  4/1984  Pfeifer et al. ................... 250/237 G
4,916,440  4/1990  Faeser et al. ......................... 345/161

*Primary Examiner*—David C. Nelms
*Assistant Examiner*—K. Shami
*Attorney, Agent, or Firm*—Nikaido, Marmelstein, Murray & Oram

[57] ABSTRACT

Disclosed is a positioning mechanism of an ophthalmologic apparatus in which the operation property of the conventional mechanical vertical movement mechanism is kept while the feature of the vertical movement by means of electrical driving source or the like is utilized. That is, a positioning mechanism of an ophthalmologic apparatus for making positioning so as to obtain a predetermined height relationship between a subject eye and a measurement system or an inspection system of the ophthalmologic apparatus, comprises: a driving means for moving the measurement system or the inspection system relative to the subject eye; an operation knob to be operated for the operation of vertical movement; a speed detection means for detecting rotating speed of the operation knob; and a control means for non-linearly controlling the quantity of driving of the driving means relative to the rotation of the rotary knob on the basis of the result of detection of the speed detection means.

8 Claims, 6 Drawing Sheets

F I G. 2
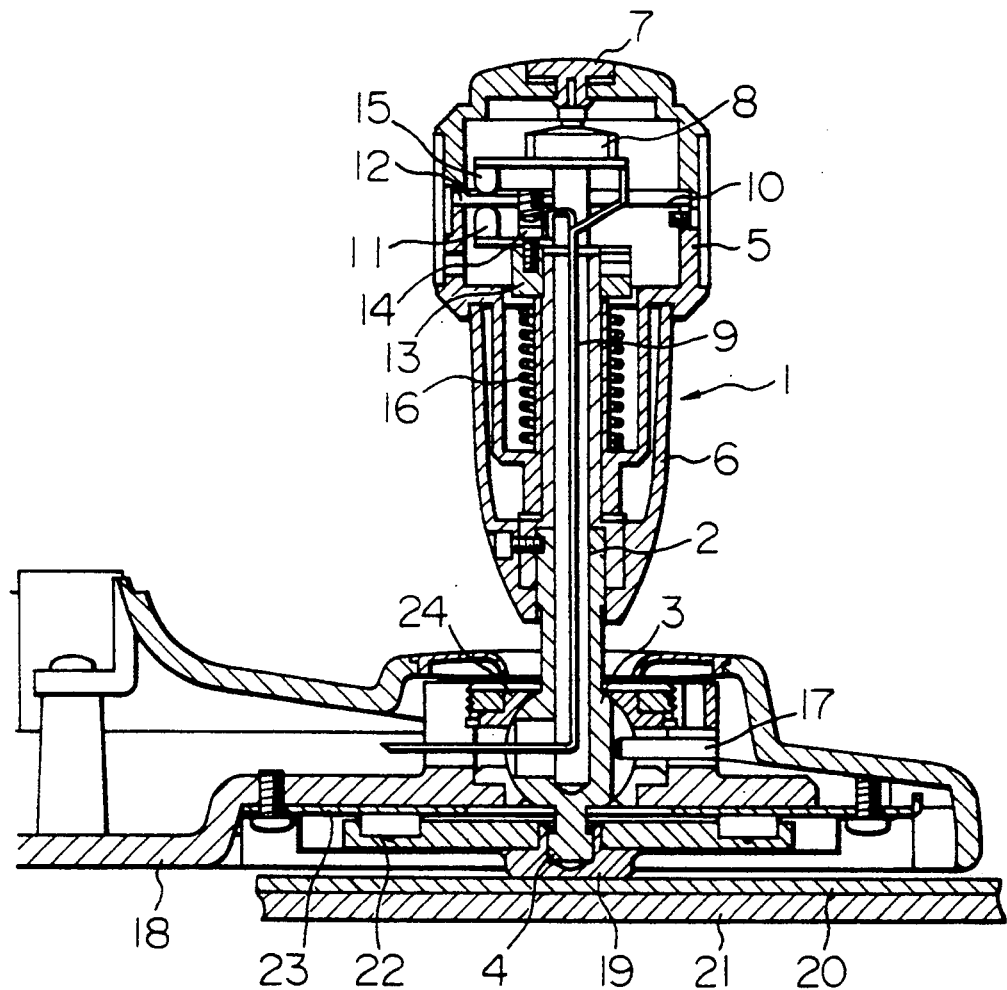
F I G. 3A    F I G. 3B
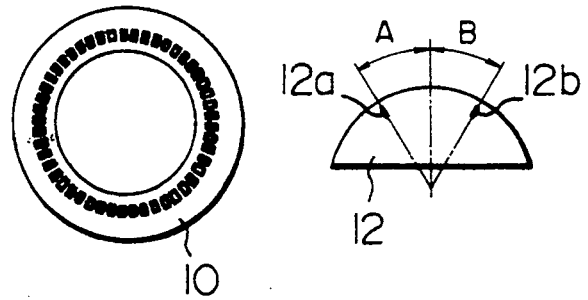

POSITIONING MECHANISM OF OPHTHALMOLOGIC APPARATUS

BACKGROUND OF THE INVENTION

1. Field of the Invention

The present invention relates to a positioning mechanism between an eye to be inspected and a measurement system or an inspection system of an ophthalmologic apparatus, and particularly relates to a mechanism for controlling an up/down (hereinafter referred to as "vertical") movement in such an ophthalmologic apparatus.

2. Description of the Related Art

In an ophthalmologic apparatus such as a fundus camera or the like, there is provided a mechanism for performing positioning of a measurement system or an inspection system relative to an eye to be inspected. The range of vertical movement required in an ophthalmologic apparatus is generally about 30 mm, and to this end, conventionally, a mechanical mechanism using a feed screw is known. That is, in such a mechanical mechanism, a rotary portion is provided on the outer periphery of an operation rod called a joy stick and the rotating movement of the rotary portion is transmitted to a vertical movement mechanism through a combination of belts and/or gears. In such a system, the relationship between the rotated angle of a vertical movement knob and the quantity of vertical feeding is fixed.

Further, in some of so-called refractometers and keratometers, there has been a proposal of a device in which a vertical movement mechanism is motor-driven. In this device, the speed can be switched between two, high and low, stages. A rotary knob is provided on the upper side of a joy stick so that a low speed vertical movement is carried out at a predetermined rotated angle of the rotary knob, while a high speed vertical movement is carried out at another predetermined rotated angle of the rotary knob.

Further, there is another example of device in which an exclusive use vertical movement knob is provided on the lower side of a joy stick so that the relationship between the quantity of rotation of the knob and the rotation number of a vertical movement motor is set so as to be linear.

The above-mentioned mechanical vertical movement mechanism has a problem in that it is complicated in structure, while it is advantageous in that the operation property is good because the relationship between the inspector's operation and the quantity of movement is linear and the speed of movement can be adjusted freely.

The above-mentioned device in which the relationship between the quantity of rotation of the knob and the rotation number of a vertical movement motor is set so as to be linear has another problem because it takes a long time for the movement to a necessary position, while the device is advantageous in that it is simple in structure. That is, in such a device as a non-contact tonometer in which strict positioning is required, it is necessary that the rotary knob is rotated many times so as to carry out vertical movement comparatively largely in the case where many subjects different in hight from one another are to be inspected successively.

Further, in the device in which the speed of vertical movement can be switched between two, low and high, speed stages, the operation is troublesome because the switching between low and high speed stages must be decided in accordance with the judgement by the inspector per se, and this device is inferior to the mechanical vertical movement mechanism in view of operation property because the content of operation and the quantity of movement are difficult to coincide with the inspector's operation sense.

Related art can be listed as follows.

Japanese Patent Examined Publication No. 3-1689; Japanese Patent Examined Publication No. 2-88028; Japanese Patent examined Publication No. 2-88029; Japanese Patent Unexamined Publication No. 61-198322; U.S. Pat. No. 4,489,303; U.S. Pat. No. 4,748,323; U.S. Pat. No. 4,794,388; U.S. Pat. No. 4,584,510; U.S. Pat. No. 4,382,166; U.S. Pat. No. 4,533,827; U.S. Pat. No. 5,113,179; U.S. Pat. No. 4,616,115; U.S. Pat. No. 4,879,556; U.S. Pat. No. 5,008,534; U.S. patent application Ser. No. 07/910060 by Masahiro Sugimura, "Joy Stick Mechanism"; and U.S. patent application Ser. No. 08/052,916 by Yoshiaki Mimura, et al "Joy Stick Mechanism for Ophthalmic Apparatus", the disclosures of the above U.S. Patent Applications are incorporated herein by reference.

SUMMARY OF THE INVENTION

In view of the above problems in the conventional techniques, an object of the present invention is to provide a positioning mechanism of an ophthalmologic apparatus in which the operation property of the conventional mechanical vertical movement mechanism is kept while the feature of the vertical movement by means of electrical driving source or the like is utilized.

BRIEF DESCRIPTION OF THE DRAWINGS

FIG. 2 is a sectional view for explaining the joy stick mechanism of this embodiment;

FIGS. 3A and 3B are views for explaining the configuration of a disc and a mask;

DESCRIPTION OF THE PREFERRED EMBODIMENTS

Figure 1:
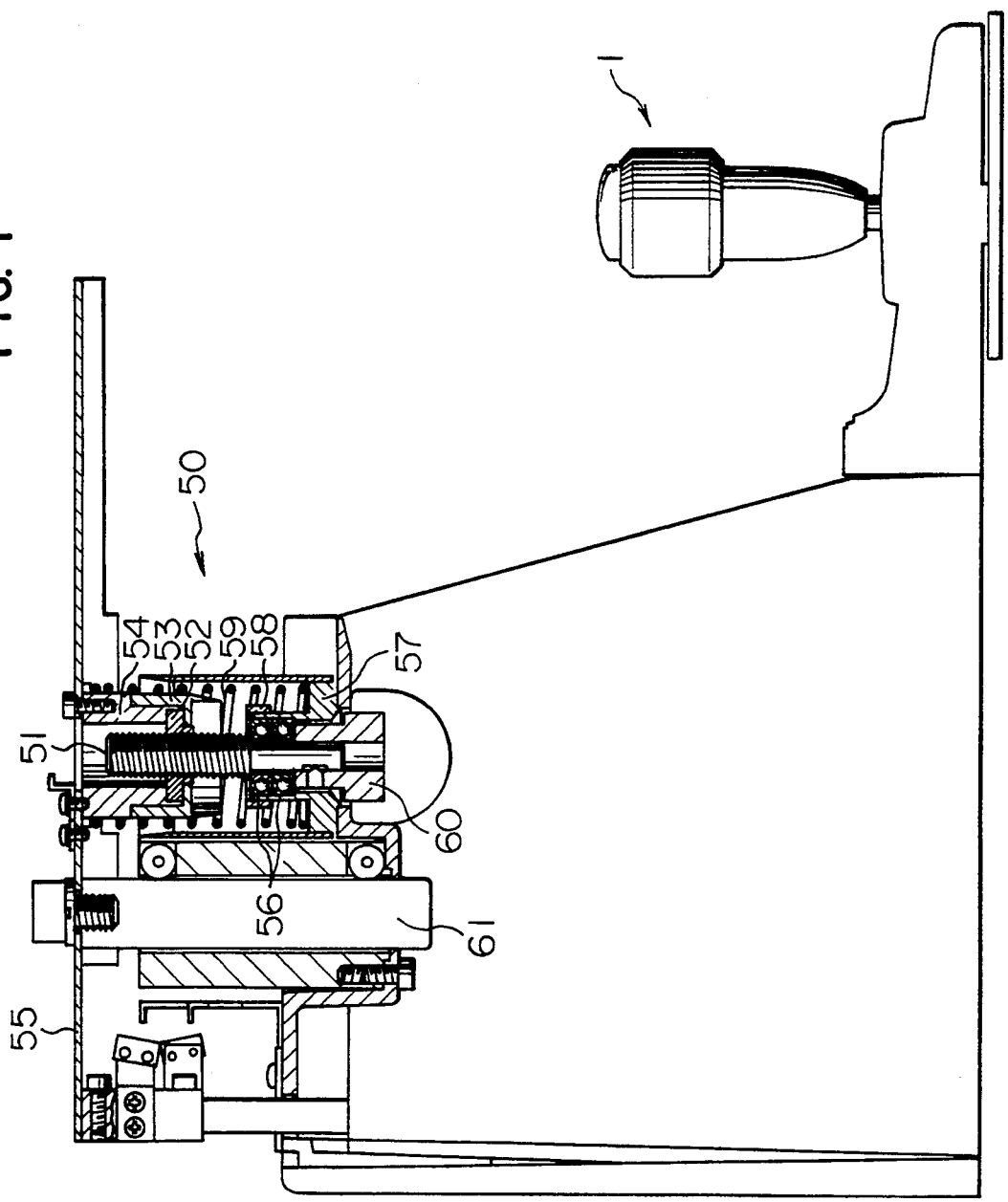
FIG. 1 is a sectional view showing a vertical movement mechanism and a joy stick mechanism.

The present invention will be described hereunder on the basis of embodiments illustrated in the drawings.

FIG. 1 is a sectional view showing a vertical movement mechanism and a joy stick mechanism, and FIG. 2 is a sectional view showing in detail the the joy stick mechanism.

A shaft 2 is inserted into a joy stick 1, and a spherical surface portion 3 and a substantially globular shape spherical surface portion 4 are formed on the lower portion of the shaft 2. A rotary knob 5 is provided so as to rotate relative of the shaft 2, and a turning knob 6 for turning the joy stick is fixedly mounted on the shaft 2. An operation button is disposed on the top portion of the rotary knob 5 and a switch 8 is fixedly provided on the turning knob 6 so that the switch 8 is operated when the operation button is pushed down, and a signal of the switch 8 is sent to a control circuit (not shown) of the apparatus through an electric wire 9 to start medical treatment, photographing, measurement, etc.

A disc 10 having a plurality of slits (FIG. 3A) is fixed on the rotary knob 5 so that the disc 10 is rotated when the rotary knob 5 is rotated. A pair of LEDs 11 are fixed on the shaft 2, a mask 12 having two slits 12a and 12b (FIG. 3B) is fixed on the shaft 2 through a nut 13 and a foot 14, and a pair of phototransistors 15 are fixed on the shaft 2 through the nut 13. The two LEDs 11 and the two phototransistors 15 are arranged in opposition to each other respectively through the disc 10 and the mask 12 and disposed in the positions corresponding to the two slits 12a and 12b of the mask 12 respectively. The two slits 12a and 12b of the mask 12 are arranged in the positions so that the respective output waveforms of the two phototransistors 15 respectively corresponding to the two slits 12a and 12b are shifted from each other by ¼ period in ON-OFF timing. The light of each LED 11 passing through the corresponding slit of the mask 12 is radiated onto the corresponding phototransistor 15 intermittently as the disc 10 rotates, and the output signals of the phototransistor 15 is sent to a control circuit of the apparatus which will be described later. The construction composed of 10, 11, 12 and 15 is called as a rotary encorder. A spring 16 for adjusting the weight of the rotary knob 5 is provided in the joy stick 1.

A pin 17 is fixed on a base 18 for mounting an optical device through a vertical movement mechanism, which will be described later, so that the pin 17 arranged in a horizontal position relative to a center point of turning of the shaft 2. The pin 17 is fitted into a slot at a lower end of the shaft 2 so as to separate the shaft 2 and the turning knob 6 in rotation.

The base 18 is movable horizontally on a friction plate 20 through a slide plate 19. The friction plate 20 is stuck on a fixed table 21. A slip plate 22 is fitted on the slide plate 19 and a plate 23 is fixed on the base 18. When the turning knob 6 is turned, the shaft 2 turns with the center of the spherical surface portion 3 as a fulcrum through a ball bearing 24 so that the lower end of the shaft 2 makes the slide plate 19 swing. If materials are selected so as to make the friction force between the slide plate 19 and the friction plate 20 is stronger than that between the plate 23 and slip plate 22, the slide plate 19 does not move when the lower end of the shaft 2 makes the slide plate 19 swing while the base 18 makes the slip plate 22 slide horizontally through the plate 23 to thereby realize a horizontal slight shock.

A vertical movement mechanism 50 has a feed screw 51. In movable side a female screw 52 is sandwiched between a female screw presser 53 and a bearing 54 and fixed on a plate 55. The vertical movement mechanism 50 has a bearing 56 and a bearing support 57, bearings presser 5 and a compression spring 59 is provided between the plate 55 and the bearing support 57. The compression spring 59 supports the load of an optical system and the like, so as to make the vertical movement of the later smooth. The female screw presser 53 also functions as a guide for the compression spring 59.

The vertical movement mechanism 50 is provided with a pulley 60 and a belt is stretched between the vertical movement mechanism 50 and another pulley which is not shown. The not-shown pulley is attached on a lower portion of a not-shown motor (36 in FIG. 4) so that when the motor is driven the pulley 60 is rotated through the not-shown pulley and the belt to thereby rotate the feed screw 51. With the rotation of the feed screw 51, the female screw 52 moves vertically along a slot formed in the feed screw 51 so that the female screw presser 53, the bearing 54 and the plate 55 which are united with the female screw 52 also move vertically. The reference numeral 61 designates a vertical movement shaft.

Figure 4:
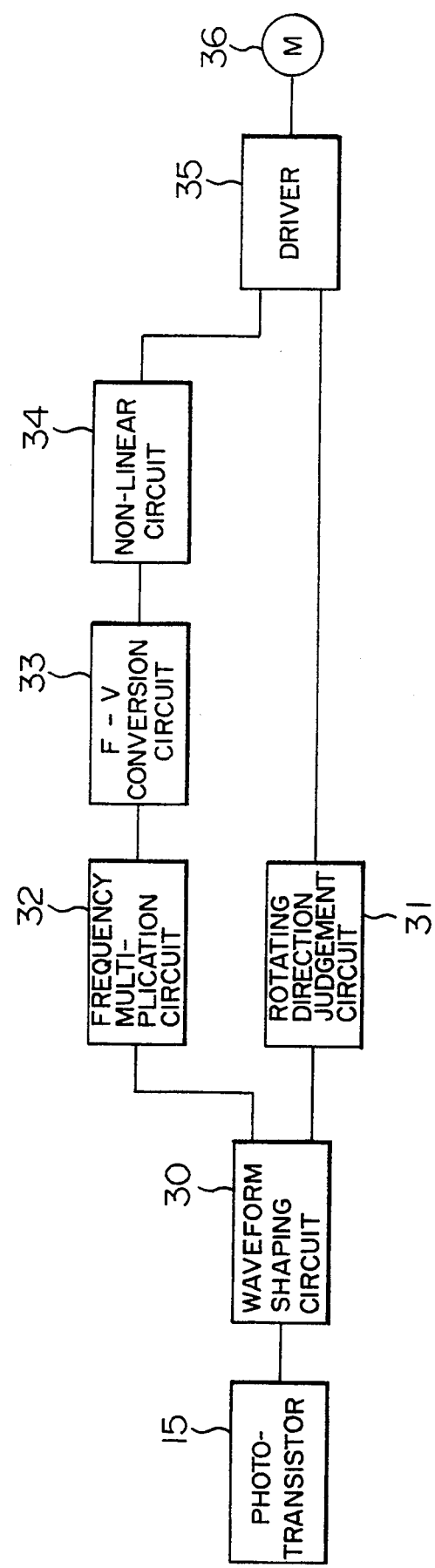
FIG. 4 is a functional block diagram showing a circuit for processing signals of phototransistors.

Next, the circuit for processing the signals of the phototransistors 15 will be described on the basis of the functional block diagram of FIG. 4.

The outputs of the phototransistors 15 are outputted as two clock pulses different in phase by 90 degrees. After waveform-shaped into rectangular waves by a waveform shaping circuit 30, the clock pulse signals are supplied to a rotating direction judgement circuit 31. The rotating direction judgement circuit 31 judges the rotating direction by detecting the output state of the waveform of one of the phototransistors 15 relative to that of the other phototransistor 15 at a preset reference point.

The output signal of the waveform shaping circuit 30 is supplied also to a frequency multiplication circuit 32. which outputs pulses the number of which is two times or four times as large as the number of slits of the disc 10. If the disc 10 has a sufficiently large number of slits, the frequency multiplication circuit 32 may be omitted.

In this embodiment, the number of slits of the disc 10 was selected to be 72 so that 288 pulses the number of which was four times as large as the number of input pulses were outputted. The number of slits 72 was selected taking the working accuracy into consideration.

Figure 5:
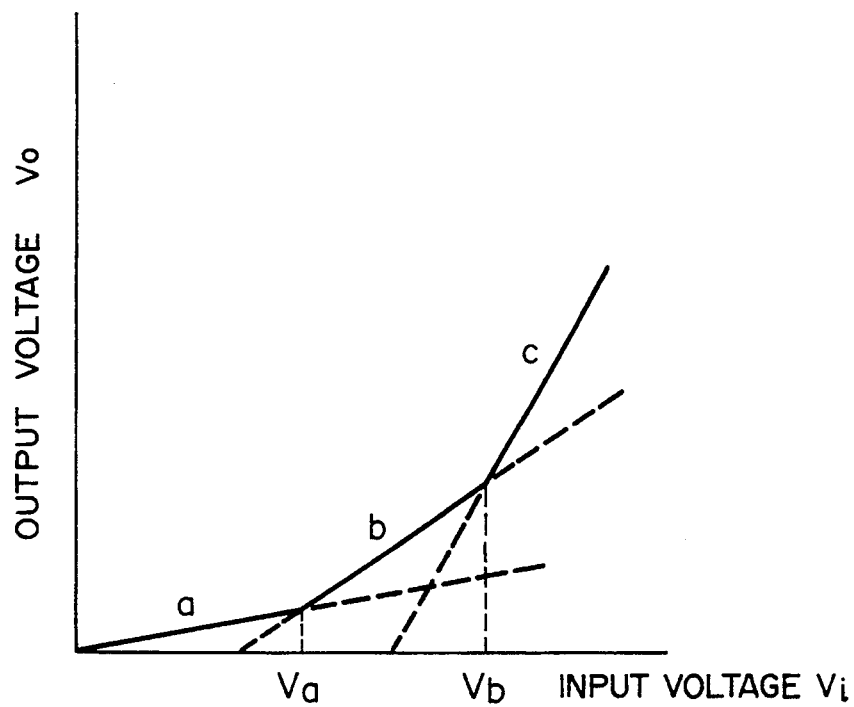
FIG. 5 is an explanatory diagram for explaining the function of the circuit of FIG. 4.
Figure 6:
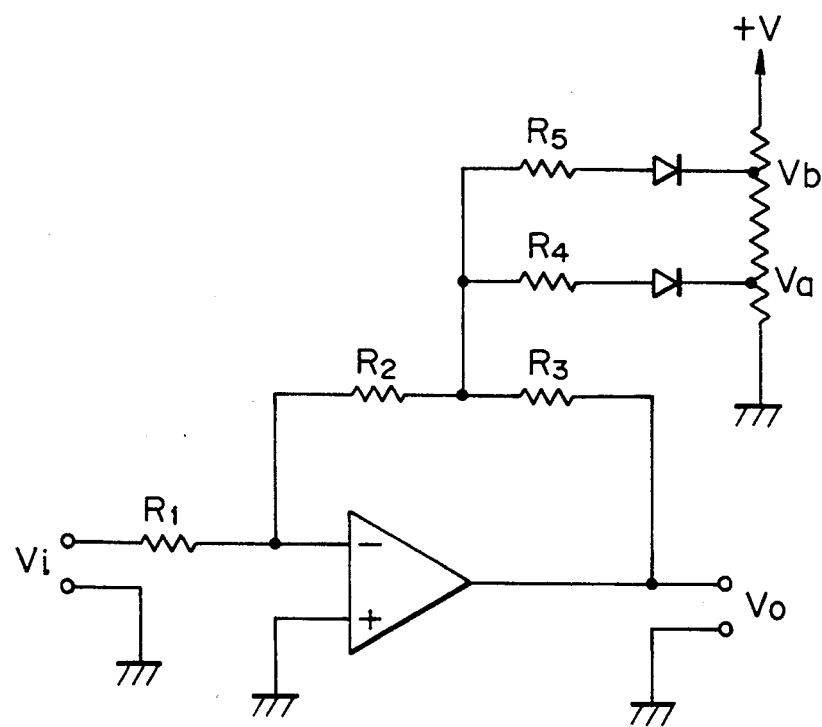
FIG. 6 is a diagram showing an example of a non-linear circuit constituted by using an operational amplifier.

The output pulses of the frequency multiplication circuit 32 are supplied to an F-V conversion circuit 33. The F-V conversion circuit 33 converts the rotating speed of the rotary knob 5 into a voltage because the rotating speed of the disc 10 corresponds to the period (frequency) of the pulses. The voltage outputted from the F-V conversion circuit 33 is supplied to a non-linear circuit 34. FIG. 5 is a diagram for explaining the function of this non-linear circuit 34. Though the input voltage is proportional to the pulse frequency, the non-linear circuit 34 functions as an amplifier with a gain shown in the region a in an input voltage range not higher than Va, with another gain shown in the region b in an input voltage range of from Va to Vb, and with a further gain shown in the region c in an input voltage range not lower than Vb. FIG. 6 is a diagram showing a specific example of the non-linear circuit 34 constituted by using an operational amplifier. In this non-linear circuit, the output voltage Vo is as follows.

In the region a: $Vo = -(R2+R3)Vi/R1$

In the region b:
$Vo = -(R2/R1)(1+R3/R4)Vi - (R3/R4)Va$

In the case of the non-linear circuit having such an input/output characteristic as shown in FIG. 5, when the rotary knob 5 is rotated slowly, the non-linear circuit drives a DC motor 36 through a driver 35 with the gain of the region a so as to finely move the vertical movement mechanism. If the rotating speed of the rotary knob 5 is increased gradually so as to enter the region b or region c, a voltage corresponding to the region is applied to the driver 35 so that the DC motor rotates quickly (moves roughly).

Figure 7:
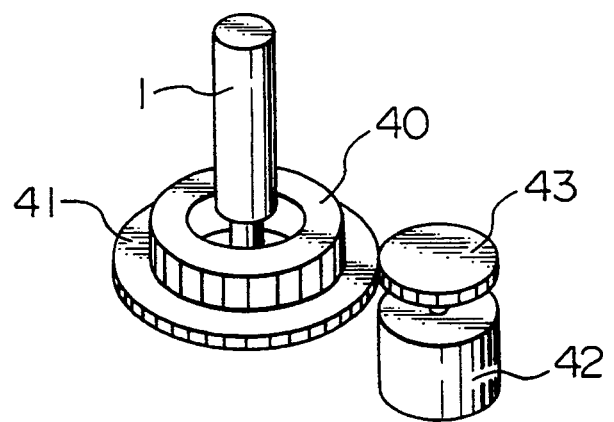
FIG. 7 is an explanatory view for explaining the position of arrangement of a rotary knob.

A second embodiment is different from the first embodiment in that the rotary knob is provided at a different position and a control circuit employing a microcomputer circuit is used. FIG. 7 is an explanatory view for explaining the position of arrangement of the rotary knob.

A rotary knob 40 is provided on the lower portion of the joy stick 1, and a gear 43 attached to a rotary encoder 42 is rotated through a gear 41 which rotates in synchronism with the rotary knob 40. In response to the rotation of the gear 43, the rotary encoder 42 generates a clock pulse signal.

Figure 8:
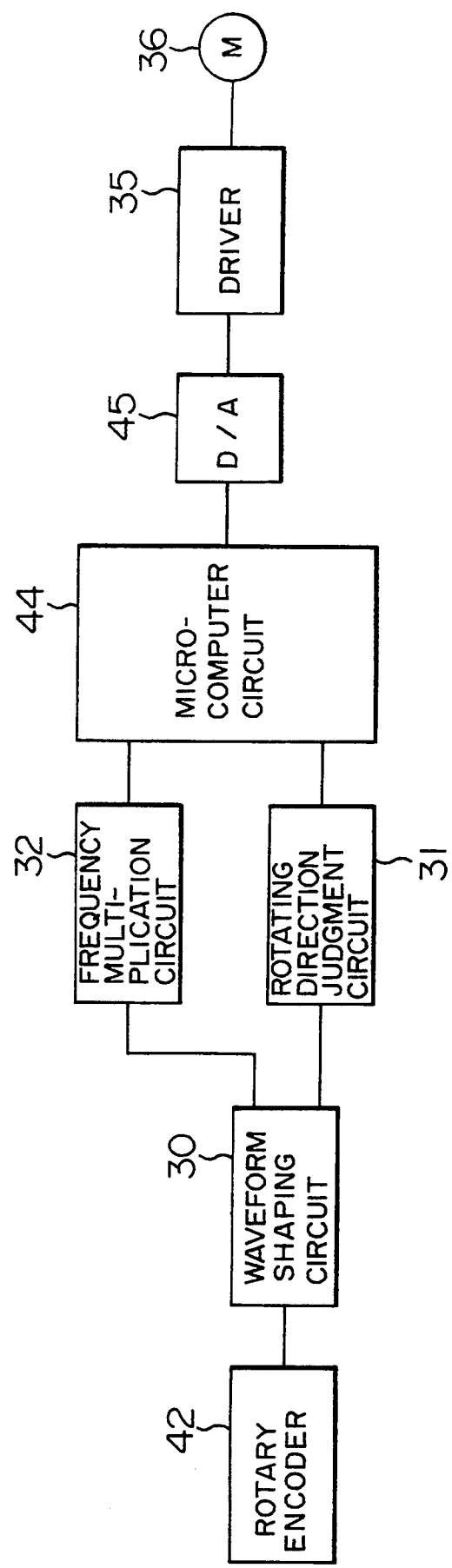
FIG. 8 is a block diagram showing a control circuit.

FIG. 8 is a block diagram showing a control circuit.

A waveform shaping circuit 30, a rotating direction judgement circuit 31 and a frequency multiplication circuit 32 are the same as those in the first embodiment. In a microcomputer circuit 44, a non-linear characteristic is incorporated as a program. The built-in non-linear characteristic may be a smooth curved function (for example, a quadratic curve, a cubic curve, an exponential curve, etc.). Alternatively, the non-linear characteristic may be stored as an input-to-output table. The microcomputer circuit 44 drives a DC motor 36 through a D/A conversion circuit 45 and a driver 35.

The above description about the second embodiment teaches the control of the driving for the motor on the basis of the rotating speed of the rotary knob. In such a case as the second embodiment using a microcomputer, it becomes possible to carry out the control more finely. For example, the control may be carried out on the basis of a combination of the rotating speed and rotated angle of the rotary knob 40 so that a voltage corresponding to the rotating speed is outputted in the case of rotation where the rotated angle exceeds a predetermined value in a predetermined time.

We claim:

1. A positioning mechanism of an ophthalmologic apparatus for adjusting a height of an optical system of said ophthalmologic apparatus relative to a subject eye, said positioning mechanism comprising:
   an operation knob to be operated by an inspector;
   a detection means for detecting an operation speed of said operation knob;
   a driving source for vertically moving said optical system of said ophthalmologic apparatus; and
   a driving source control means for non-linearly increasing the ratio of the driving speed of said driving source to the operation speed detected by said detection means.

2. A positioning mechanism of an ophthalmologic apparatus for adjusting a height of an optical system of said ophthalmologic apparatus relative to a subject eye, said positioning mechanism comprising:
   (a) an operation knob having a grasping portion which is rotatable around a shaft;
   (b) a detection means for detecting a rotating direction and a rotating speed of said operation knob;
   (c) a driving motor for vertically moving said optical system of said ophthalmologic apparatus; and
   (d) a driving motor control means for non-linearly increasing the ratio of the driving speed of said driving motor to the rotating speed obtained by said detection means.

3. A positioning mechanism of an ophthalmologic apparatus according to claim 2, wherein said detection means includes a rotary encoder and a signal processing circuit.

4. A positioning mechanism of an ophthalmologic apparatus according to claim 2, wherein said control means includes a segment-like non-linear circuit using an operational amplifier.

5. A positioning mechanism of an ophthalmologic apparatus according to claim 2, wherein said control means includes a microcomputer.

6. A positioning mechanism of an ophthalmologic apparatus according to claim 2, wherein said operation knob includes a joy stick bar for roughly and finely moving a base for mounting said ophthalmologic apparatus.

7. A positioning mechanism of an ophthalmologic apparatus for adjusting a height of an optical system of said ophthalmologic apparatus relative to a subject eye, said positioning mechanism comprising:
   (a) an operation knob having a grasping portion which is rotatable about a center shaft;
   (b) a disc having radial slots and being rotated in synchronism with the rotation of said grasping portion of said operation knob;
   (c) pairs of light-emitting and light-detecting devices, each pair including a light emitting device and a light detecting device in opposition with each other with said disc interposed therebetween, said pairs of light-emitting and light-detecting devices being disposed in positions so that waveforms of the respective outputs of said pairs of light-emitting and light-detecting device are shifted in phase from each other and so that said pairs of light-emitting and light-detecting devices are independent of the rotation of said grasping portion;
   (d) a processing means for obtaining a rotating direction and a rotating speed of said operation knob from the waveforms of the respective outputs of said light detecting devices of said pairs of light-emitting and light-detecting device;
   (e) a driving motor for vertically moving said optical system of said ophthalmologic apparatus; and
   (f) a driving motor control means for non-linearly increasing the ratio of the driving speed of said driving motor to the rotating speed obtained by said processing means.

8. A positioning mechanism of an ophthalmologic apparatus according to claim 7, wherein a mask having slits is interposed between said light detecting devices and said disc.

* * * * *